US007273467B1

(12) United States Patent
Mezzoli

(10) Patent No.: US 7,273,467 B1
(45) Date of Patent: Sep. 25, 2007

(54) DEVICE FOR WASHING THE EXTERNAL AUDITORY MEATUS

(76) Inventor: Giorgio Mezzoli, Via Ricci Curbastro, 56/I-48022 Lugo (IT)

( * ) Notice: Subject to any disclaimer, the term of this patent is extended or adjusted under 35 U.S.C. 154(b) by 1193 days.

(21) Appl. No.: 10/031,967

(22) PCT Filed: Jul. 25, 2000

(86) PCT No.: PCT/EP00/07110

§ 371 (c)(1),
(2), (4) Date: Apr. 26, 2002

(87) PCT Pub. No.: WO01/07100

PCT Pub. Date: Feb. 1, 2001

(30) Foreign Application Priority Data

Jul. 26, 1999 (IT) .......................... MI99A1639

(51) Int. Cl.
*A61M 3/00* (2006.01)

(52) U.S. Cl. .............................. 604/43; 604/39; 604/41; 604/275

(58) Field of Classification Search .................... 604/19, 604/21, 39, 41, 43, 44, 45, 264, 275, 289, 604/290; 600/563; 606/162
See application file for complete search history.

(56) References Cited

U.S. PATENT DOCUMENTS

| 1,845,343 | A | * | 2/1932 | Salerni ......................... 604/32 |
| 2,421,294 | A | * | 5/1947 | Shotton ......................... 604/30 |
| 2,494,088 | A | * | 1/1950 | Dulity ........................... 604/39 |
| 2,576,766 | A | * | 11/1951 | Sokolik ......................... 604/37 |
| 2,879,768 | A | * | 3/1959 | Anderson ...................... 604/39 |
| 3,835,842 | A | * | 9/1974 | Iglesias ....................... 600/105 |
| 3,850,175 | A | * | 11/1974 | Iglesias ....................... 606/46 |
| 4,206,756 | A | | 6/1980 | Grossan |
| 5,221,255 | A | * | 6/1993 | Mahurkar et al. ............ 604/43 |
| 5,221,256 | A | * | 6/1993 | Mahurkar ..................... 604/43 |
| 5,364,343 | A | | 11/1994 | Apolet et al. |
| 5,395,316 | A | * | 3/1995 | Martin ......................... 604/43 |
| 5,451,206 | A | * | 9/1995 | Young .......................... 604/43 |
| 6,155,987 | A | * | 12/2000 | Scherl ......................... 600/562 |

FOREIGN PATENT DOCUMENTS

| EP | 502 485 A1 | 9/1992 |
| FR | 2 726 476 | 11/1994 |

* cited by examiner

*Primary Examiner*—Nicholas Lucchesi
*Assistant Examiner*—Jeremy Thissell
(74) *Attorney, Agent, or Firm*—Morgan & Finnegan, LLP

(57) ABSTRACT

A device is described for washing the external audtitory meatus comprising at least ne inlet channel (6) for the washing liquid and one discharge channel (8) which connects the end portion of the inlet channel with the outside environment, the discharge channel being designed to discharge the washing liquid outside if a further channel(9), designed to discharged the liquid and the products of washing (wax, epithelial scales, etc.) outside, is at least partially obstructed by the products of washing. The further channel may consist of the external auditory meatus, of an aural speculum in which the washing device (10) is inserted, or f an outlet channel made in the body of the washing device (10).

18 Claims, 6 Drawing Sheets

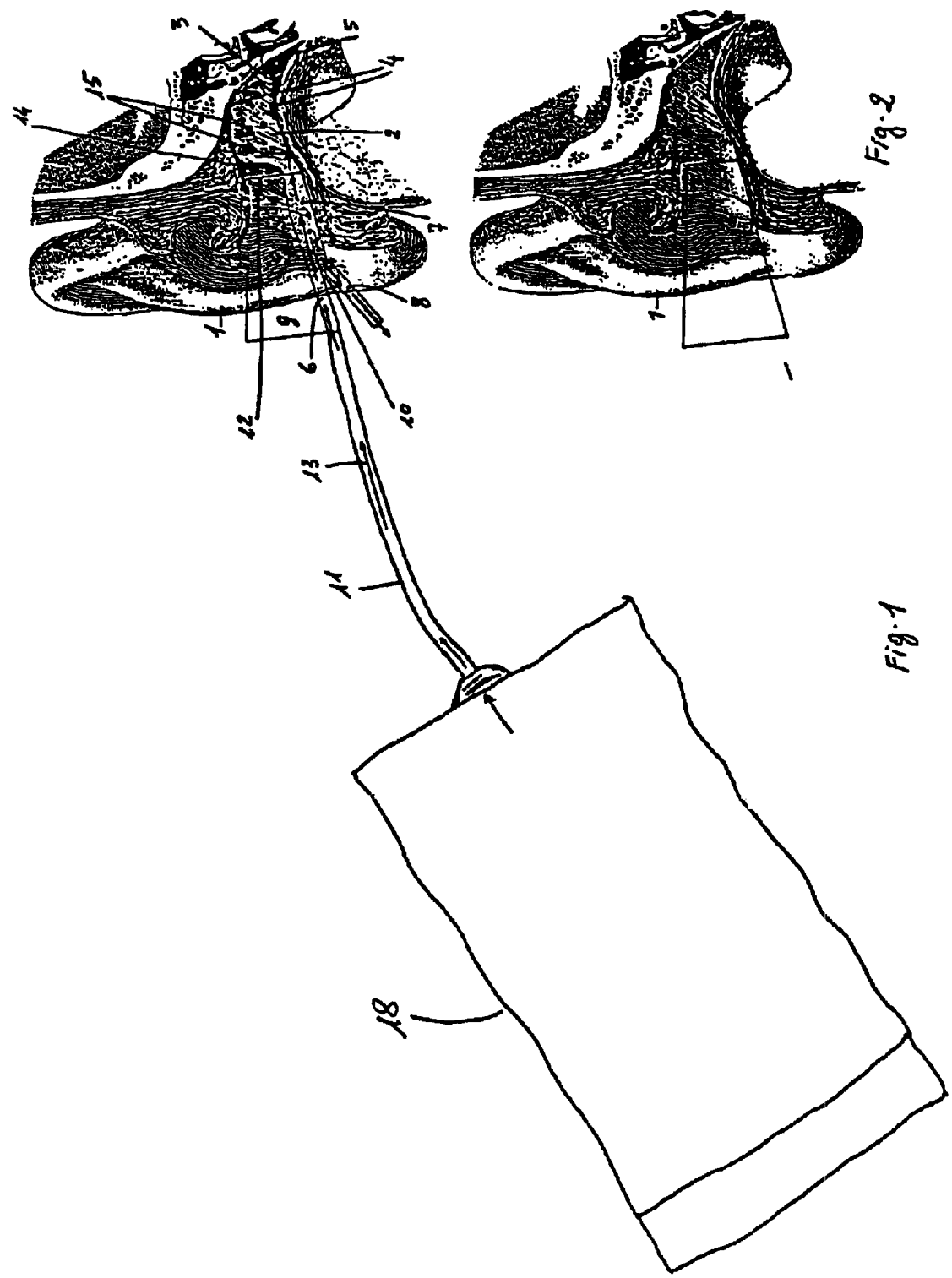

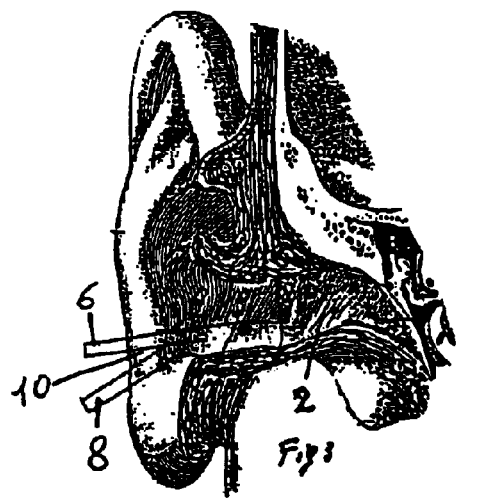
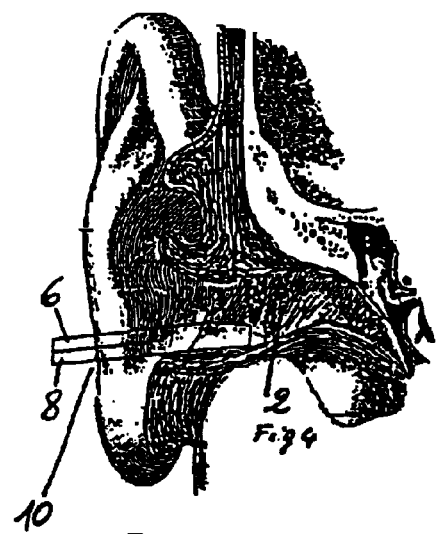
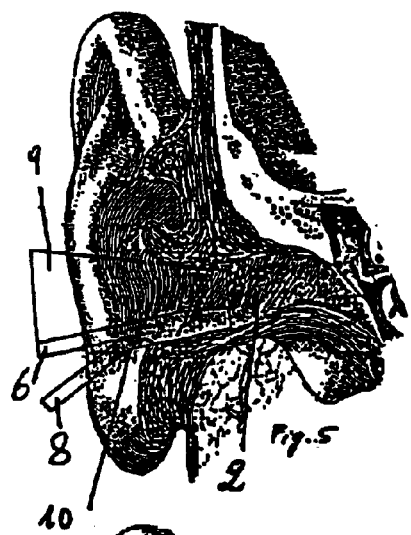
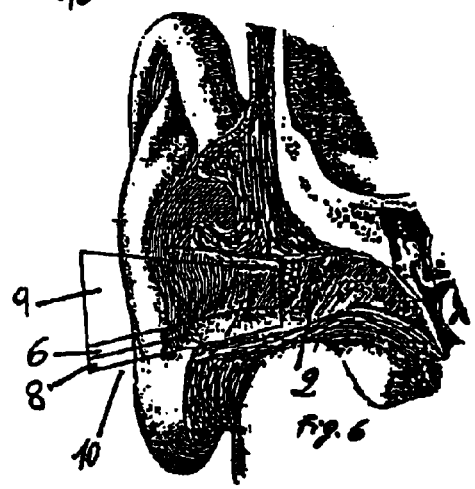
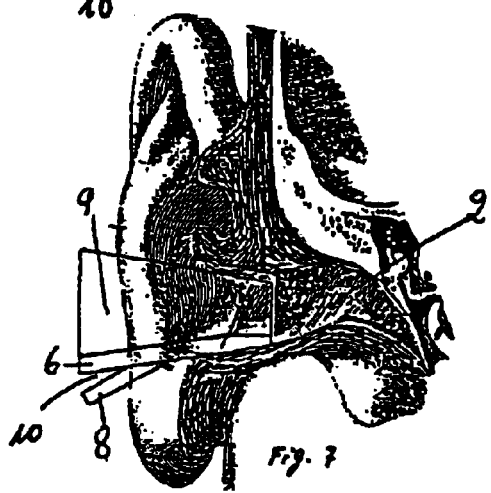
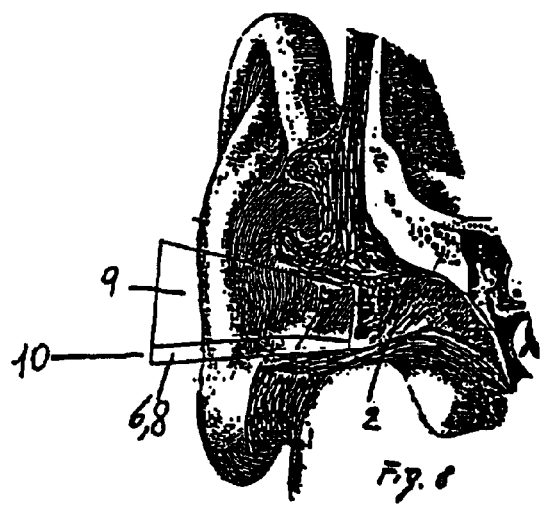

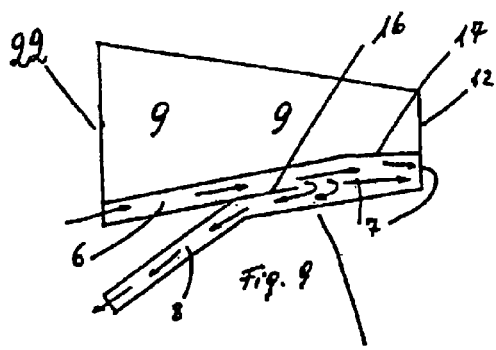 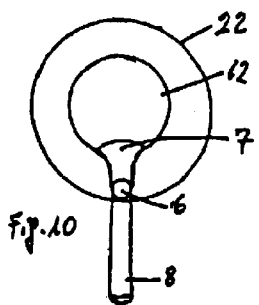 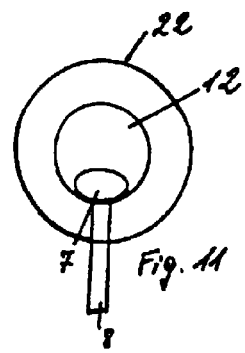
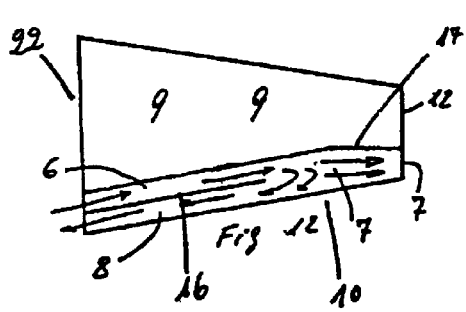 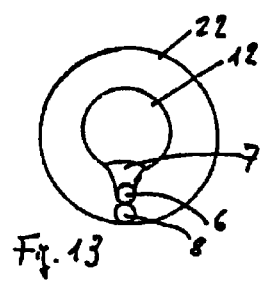 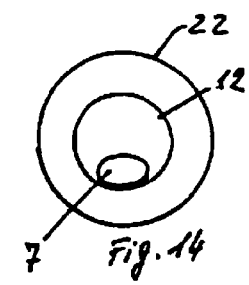
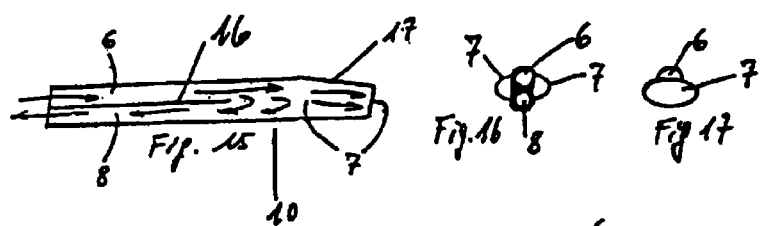
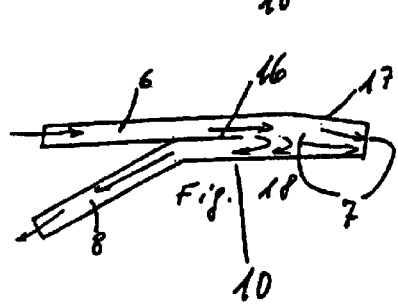 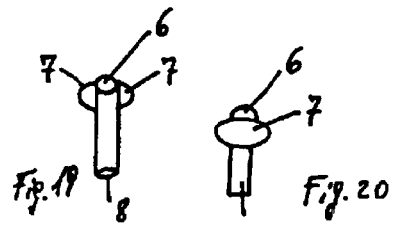

DEVICE FOR WASHING THE EXTERNAL AUDITORY MEATUS

SCOPE OF THE INVENTION

The invention consists of a device for washing the external auditory meatus comprising at least one inlet channel for the washing liquid and one discharge channel which connects the end portion of the Inlet channel with the outside environment, in which the discharge channel is designed to discharge the washing liquid outside if a further channel, designed to discharge the liquid and the products of washing (wax, epithelial scales, etc.) outside, is at least partially obstructed by the products of washing.

The further channel may consist of the external auditory meatus, of an aural speculum in which the washing device is inserted, or of an outlet channel made in the body of the washing device.

PRIOR ART

Devices are known and available on the market that normally comprise at least one inlet channel and one outlet channel, designed to introduce (for purposes of hygiene, prevention and/or for treatment of possible affections) a liquid product of appropriate characteristics and/or composition (referred to in what follows as "a liquid") into the external auditory meatus and/or into other body cavities accessible from outside. The active substances (possibly) present in the liquid vary (or may vary) in each case according to the specific purpose for which the liquid is designed and will not be further discussed herein because they are in any case extraneous to the present invention.

In particular, the known devices for washing the external auditory meatus have an inlet channel for the washing liquid, the section of which is smaller than that of the outlet channel through which the liquid and the products of washing (wax, epithelial scales, etc.) are discharged outside. In this way it is possible to avoid that the amount of washing liquid introduced into the external auditory meatus (normally at a pressure slightly higher than atmospheric pressure to obtain a more effective action of disgregation and of removal of the wax) may be greater than that coming out through the outlet channel, thus creating an overpressure in the external auditory meatus that is (at least potentially) dangerous for the integrity and/or the functionality of the tympanic membrane.

The products of washing, disgregated and removed from the walls of the external auditory meatus by the action of the liquid, are normally carried by the liquid itself into the outlet channel and discharged outside. However, if their dimensions are comparable to (or larger than) those of the access hole to the outlet channel, they may obstruct said channel (at least partially), thus reducing the space available for the outflow of the liquid and of the products of washing and giving rise, in the external auditory meatus, against the tympanic membrane, to an overpressure of the washing liquid which is (at least potentially) dangerous for the integrity and/or functionality of the membrane itself, and which could in addition damage the inner ear, with onset of tinnitus aurium and/or impairment of hearing and reduction of auditive capacity.

The risk of an overpressure of the washing liquid is particularly important if a washing device of a known type is used directly by a patient for washing the external auditory meatus (self-washing) without resorting to the assistance of qualified personnel or, in any case, of a second person (washing by others), since in this case the patient is not able to control directly and continuously the regular outflow of the liquid and of the products of washing and to suspend introduction of the washing liquid into the external auditory meatus as soon as there arises (or could arise) an anomalous situation that is (at least potentially) dangerous.

The aforesaid risk may arise also in the case of washing carried out by others if the person performing the washing operation falls to detect in time (for any reason) a situation that is (at least potentially) dangerous and/or fails to react with due promptness.

With the purpose of avoiding the risk of an overpressure of the washing liquid, a device has been proposed having three lateral- grooves as exit means (U.S. Pat. No. 4,206,756). But the design of said grooves is not such to exclude the possibility that all said grooves are obstructed by the solid products of washing.

This constitutes a serious drawback of known washing devices, which limits (or may limit) their use, in particular for self-washing of the external auditory meatus. The washing device that forms the subject of the present invention comprises means designed to prevent occurrence of the aforesaid overpressure, which render the device free from the serious drawbacks and risks of the known washing devices.

SUMMARY OF THE INVENTION

The subject of the present invention is a device for washing the external auditory meatus, comprising an inlet channel for the washing liquid and a discharge channel which connects the end portion of the inlet channel with the outside environment, in which the discharge channel is designed to discharge the washing liquid outside if a further channel, designed to discharge the liquid and the products of washing outside, is at least partially obstructed by the products of washing.

The further channel may consist of the external auditory meatus, of an aural speculum in which the washing device is inserted, or of an outlet channel made in the body of the washing device.

LIST OF FIGURES

The invention will now be described in greater detail with reference to non-limiting examples of embodiments illustrated in the attached figures, in which:

FIG. 1 is a schematic sectional view of a first embodiment of a washing device according to the invention, inserted in the external auditory meatus;

FIG. 2 is a schematic sectional view of an aural speculum inserted in the external auditory meatus;

FIGS. 3 and 4 are schematic sectional views of a second embodiment of a washing device according to the invention, inserted in the external auditory meatus;

FIG. 5 illustrates the washing device of FIG. 1, without the means designed to supply the washing liquid;

FIGS. 6–8 are schematic representations of some variants of the washing device of FIG. 5;

FIGS. 9–11 are schematic representations of a longitudinal sectional view and two front views (taken at the ends) of the washing device of FIG. 5;

FIGS. 12–14 are schematic representations of a longitudinal sectional view and two front views (taken at the ends) of the washing device of FIG. 6;

FIGS. 15–17 are schematic representations of a longitudinal sectional view and two front views (taken at the ends) of the washing device of FIG. 4;

FIGS. 18–20 are schematic representations of a longitudinal sectional view and two front views (taken at the ends) of the washing device of FIG. 3;

In the attached figures, the corresponding elements will be identified using the same reference numbers.

DETAILED DESCRIPTION

Figure 21:
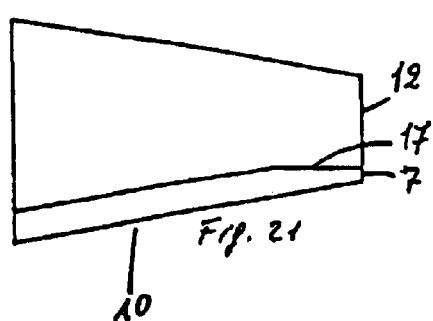
FIGS. 21–23 are schematic representations of a longitudinal sectional view and two front views (taken at the ends) of the washing device of FIG. 8.

FIG. 1 is a schematic sectional view of a first embodiment of a washing device 10, made according to the invention, inserted in the external auditory meatus and associated to means (consisting in FIG. 1 of the bag 18, particularly suited for self-washing) containing the washing liquid 13 and connected to the washing device 10 by the tube 11.

In FIG. 1 are shown the auricle 1, the external auditory meatus 2, delimited by the walls 4 and closed by the tympanic membrane 3, and pieces of wax 15 that adhere to the inner wall 4 of the external auditory meatus 2, and pieces of wax 5 that adhere to the tympanic membrane 3.

The washing device 10 (illustrated very schematically and in "see-through" view in FIG. 1) comprises an inlet channel 6 for the washing liquid 13 and a discharge channel 8, which connects the end portion 7 of the inlet channel 6 with the outside environment for discharging the washing liquid 13 outside, if a further channel 9 (referred to as "the outlet channel"), which is made in the body of the washing device 10 and is designed to discharge the liquid 13 and the products of washing 14 (consisting of at least one piece of wax) outside, is at least partially obstructed by the products of washing 14.

The section of the end portion 7 of the inlet channel 6 is greater than that of the initial portion of the inlet channel 6. Preferably, the section of the end portion 7 of the inlet channel 6 is not smaller than the section of the initial portion of the inlet channel 6 increased by the section of the discharge channel 8.

Operation of the washing device 10 will now be briefly described with reference to FIG. 1.

In conditions of normal operation, the washing liquid 13 arrives through the tube 11 (connected to the external container 18 or to possible pumping means) to the inlet channel 6, flows through the latter and (via the end portion 7 of the inlet channel 6) arrives inside the external auditory meatus 2 with sufficient energy to disgregate and remove the bits of wax 15 adhering to the inner wall 4 of the external auditory meatus 2, as well as the wax 5 that has possibly accumulated against the tympanic membrane 3, without irritating the inner wall 4 of the external auditory meatus 2 and/or damaging the tympanic membrane 3.

Only an altogether negligible amount of the washing liquid 13 introduced in the inlet channel 6 escapes through the discharge channel 8.

The products of washing 14, i.e., the bits of wax removed from the inner wall 4 of the external auditory meatus 2 and/or from the region of the tympanic membrane 3 are carried by the washing liquid 13 into the outlet channel 9 through its entrance 12, and "discharged" outside.

It is to be noted that the section of the outlet channel 9 is greater than the section of the inlet channel 6. This enables a convenient outflow of the liquid 13 and of the products of washing 14, although the outlet channel 9 is kept sufficiently pervious to maintain the pressure of the washing liquid in the external auditory meatus 2 in equilibrium with the external pressure, and hence prevent any risk that in the external auditory meatus 2 there may be an overpressure which is (at least potentially) dangerous for the functionality and/or integrity of the tympanic membrane 3.

If, as illustrated in FIG. 1, at least one of the products of washing 14 has dimensions such as to obstruct (almost) completely the entrance 12 of the outlet channel 9, thus preventing the liquid 13 entering the external auditory meatus 2 through the channel 6 from flowing out through the outlet channel 9, the liquid 13 flows out freely through the discharge channel 8, without there being any risk that in the external auditory meatus 2 an overpressure of the washing liquid may be set up that is (at least potentially) dangerous for the functionality and/or integrity of the tympanic membrane 3.

To this purpose, the section of the discharge channel 8 must not be smaller than that of the initial portion of the inlet channel 6.

In the washing device 10 illustrated in FIG. 1, the end portion of the discharge channel 8 engages laterally in the body of the washing device 10, from which it protrudes. Said protruding end portion may advantageously constitute the grip of the washing device 10 and may be connected to a tube (not illustrated in FIG. 1 for simplicity of graphical representation) so as to dispose, into a basin (or some other container), of the washing liquid 13 that flows out of by the discharge channel 8.

In FIG. 1 the flow of the liquid 13 in the tube 11, in the inlet channel 6, in the end portion 7, and in the discharge channel 8 are schematically represented by means of arrows.

Further washing devices 10 made according to the invention will be described in what follows, with reference to one or more of the attached figures.

FIG. 2 is a schematic sectional view of an aural speculum, inserted in the external auditory meatus 2, which may be used in combination with a second embodiment of the washing device 10, described in FIG. 3 (more clearly visible in FIGS. 18–20), FIG. 4 (more clearly visible in FIGS. 15–17), FIGS. 24–26 or FIGS. 30–32, which comprises only the inlet channel 6 and the discharge channel 8. The outlet channel 9 consists of the portion of the aural speculum that is not occupied by the washing device 10.

FIGS. 3 and 4 illustrate schematically, in sectional view, inserted in the external auditory meatus 2, the second embodiment of the washing device 10 according to the invention, which differs from the one described with reference to FIG. 1 essentially in that the outlet channel 9 consists of the external auditory meatus 2. All the considerations previously made with reference to FIG. 1 apply to the washing device 10 (with possible variants that are obvious for a person skilled in the branch).

In the washing device 10 of FIG. 3 (more clearly visible in FIGS. 18–20), the inlet channel 6 and the discharge channel 8 are set one over the other, and the end portion of the discharge channel 8 engages laterally in the body of the washing device 10, from which it protrudes. In the washing device 10 of FIG. 4 (more clearly visible in FIGS. 15–17) the inlet channel 6 and the discharge channel 8 are set one over the other and parallel to one another.

FIG. 5 illustrates the washing device 10 of FIG. 1 without the bag 18 that supplies the washing liquid 13. FIGS. 6–8 are schematic representations of some variants of the washing device 10 of FIG. 5, to which there apply (with possible variants that are obvious for a person skilled in the branch) all the considerations previously developed with reference to FIG. 1.

In the washing device 10 of FIG. 5 (more clearly visible in FIGS. 9–11), the inlet channel 6 and the discharge channel 8 are set one over the other, and the end portion of the discharge channel 8 engages laterally in the body of the washing device 10.

In the washing device 10 of FIG. 6 (more clearly visible in FIGS. 12–14), the inlet channel 6 and the discharge channel 8 are set one over the other and parallel to one another.

In the washing device 10 of FIG. 7 (more clearly visible in FIGS. 27–29), the inlet channel 6 and the discharge channel 8 are set alongside one another, and the end portion of the discharge channel 8 engages laterally in the body of the washing device 10.

In the washing device 10 of FIG. 8 (more clearly visible in FIGS. 21–23), the inlet channel 6 and the discharge channel 8 are set alongside one another and parallel to one another.

FIGS. 9–11 illustrate schematically a longitudinal section and two front views of the washing device 10 of FIG. 5.

FIG. 9 is a schematic representation of a longitudinal section of the washing device 10 of FIG. 5. FIG. 9 shows the outlet channel 9 made in the body of the washing device 10, the entrance 12 and the exit 22 of the outlet channel 9, the inlet channel 6 and the discharge channel 8, set over the inlet channel 6, which connects the end portion 7 of the inlet channel 6 with the outside environment.

FIG. 9 also shows the septum 16 (having a length smaller than that of the washing device 10) which separates the inlet channel 6 from the discharge channel 8 and delimits the end portion 7 of the inlet channel 6, the presence of which is necessary and in any case advantageous.

In fact, if the end portion 7 of the inlet channel 6 were omitted, the entrance of the discharge channel 8 would be aligned with the entrance 12 of the outlet channel 9: a very large product of washing 14 could obstruct (almost) completely, in addition to the entrance 12 of the outlet channel 9, also the entrance of the discharge channel 8, thus preventing the liquid 13 that enters the external auditory meatus 2 through channel 6 from flowing off both through the outlet channel 9 and through the discharge channel 8, with consequent concrete risk that in the external auditory meatus 2 there will be set up an overpressure of the washing liquid that is (at least potentially) dangerous for the integrity and/or functionality of the tympanic membrane 3.

In addition, when the liquid 13 reaches the end portion 7 (the section of which is greater than that of the initial portion of the inlet channel 6) to be introduced into the external auditory meatus 2, its pressure is reduced, thus reducing the risk that the jet of liquid 13 might irritate the inner walls 4 of the xternal auditory meatus 2 and/or damage the tympanic membrane 3.

At the exit of the end portion 7 of the inlet channel 6, there are (preferably) present means 17 designed to deflect towards the inner wall 4 of the external auditory meatus 2 the jet of liquid 13 coming out of the washing device 10 (thus eliminating any risk that the said jet might impinge directly on the tympanic membrane 3, damaging it) and, possibly, to direct and/or widen and/or flatten said jet, hence improving its capacity to disgregate and remove the fragments of wax 15 and 5, which adhere, respectively, to the inner wall 4 of the external auditory meatus 2 and to the tympanic membrane 3.

As in FIG. 1, in FIG. 9 the flow of the liquid 13 in the inlet channel 6, in the end portion 7, and in the discharge channel 8 are schematically represented by means of arrows.

FIG. 10 is a schematic representation of a front view of the aforesaid washing device 10 of FIG. 5 taken at the end of the device that remains outside the ear. FIG. 10 shows the entrance 12 and the exit 22 of the outlet channel 9, the inlet channel 6, the tip of its end portion 7, and the end portion of the discharge channel 8 that protrudes from the body of the washing device 10, of which it may advantageously constitute the grip.

FIG. 11 is a schematic representation of a front view of the washing device 10 of FIG. 5 taken at the end of the device itself to be inserted in the external auditory meatus. FIG. 11 shows the entrance 12 and the exit 22 of the outlet channel 9, the end portion of the discharge channel 8 that protrudes from the body of the washing device 10, and the tip of the end portion 7 of the inlet channel 6 which, on account of the presence of the deflecting means 17, has a preferably elliptical or flattened shape.

FIGS. 12–14 are a schematic longitudinal sectional view and two front views of the washing device 10 of FIG. 6 that differs from the one illustrated in FIG. 5 exclusively in that the discharge channel 8 is parallel throughout its length to the inlet channel 6. To FIGS. 12–14 apply (with possible variants that are obvious for a person skilled in the branch) all the considerations previously developed with reference to FIGS. 9–11.

FIGS. 15–17 are schematic representations of a longitudinal sectional view and two front views of the washing device 10 of FIG. 4.

FIG. 15 is a schematic representation of a longitudinal section of the washing device 10 of FIG. 4. FIG. 15 shows the inlet channel 6, the discharge channel 8 (set over the inlet channel, 6 from which it is separated by the septum 16) which connects the end portion 7 of the inlet channel 6 with the outside environment, and the deflecting means 17 set at the exit from the end portion 7 of the inlet channel 6.

As in FIGS. 9–12, in FIG. 15 the flow of the liquid 13 in the inlet channel 6, in the end portion 7, and in the discharge channel 8 are schematically represented by means of arrows.

FIG. 16 is a schematic representation of a front view of the washing device 10 of FIG. 4 taken at the end of the device itself that remains outside the ear. FIG. 16 shows the inlet channel 6, its end portion 7 and the discharge channel 8 set one over the other.

FIG. 17 is a schematic representation of a front view of the washing device 10 of FIG. 4 taken at the end of the device itself to be inserted in the external auditory meatus. FIG. 17 shows the top wall of the end portion 7 of the inlet channel 6, which on account of the presence of the deflecting means 17 has preferably an elliptical or flattened shape.

FIGS. 18–20 are schematic representations of a longitudinal sectional view and two front views of the washing device 10 of FIG. 3, which differs from the one illustrated in FIG. 4 exclusively in that the end portion of the discharge channel 8 protrudes from the body of the washing device 10, of which it may advantageously constitute the grip. To FIGS. 18–20 apply (with possible variants that are obvious for a person skilled in the branch) all the considerations previously developed with reference to FIGS. 15–17.

Figure 22:
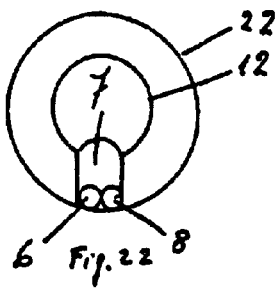
Figure 23:
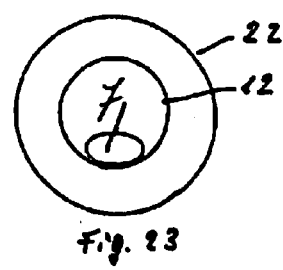

FIGS. 21–23 are schematic representations of a longitudinal sectional view and two front views of the washing device 10 of FIG. 8, which differs from the one illustrated in FIG. 6 exclusively in that the discharge channel 8 is set alongside the inlet channel 6, to which it is parallel throughout its length. To FIGS. 21–23 apply (with possible variants that are obvious for a person skilled in the branch) all the considerations previously developed with reference to FIGS. 9–11.

Figure 24:
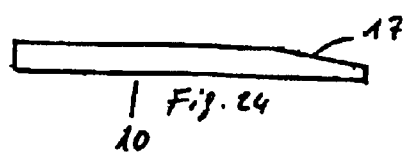
FIGS. 24–26 are schematic representations of a side view and two front views (taken at the ends) of a variant of the washing device of FIG. 4.
Figure 25:
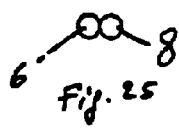
Figure 26:
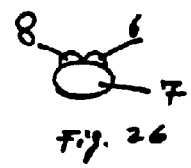

FIGS. 24–26 are schematic representations of a side view and two front views of a variant of the washing device 10 of FIG. 4, from which it differs exclusively in that the discharge channel 8 is set alongside the inlet channel 6, to which it is parallel throughout its length. To FIGS. 24–26 apply (with possible variants that are obvious for a person skilled in the branch) all the considerations previously developed with reference to FIGS. 15–17.

Figure 27:
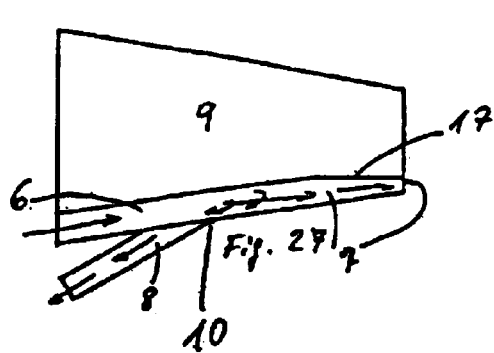
FIGS. 27–29 are schematic representations of a sectional side view and two front views (taken at the ends) of the washing device of FIG. 7.
Figure 28:
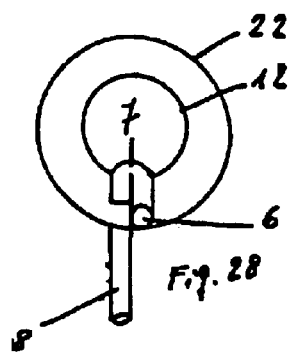
Figure 29:
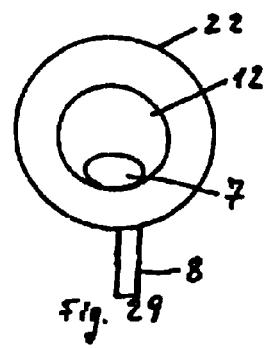

FIGS. 27–29 are schematic representations of a longitudinal sectional view and two front views of the washing device 10 of FIG. 7, which differs from the one illustrated in FIG. 5 exclusively in that the discharge channel 8 is set alongside the inlet channel 6. To FIGS. 27–29 apply (with possible variants that are obvious for a person skilled in the branch) all the considerations previously developed with reference to FIGS. 9–11.

Figure 30:
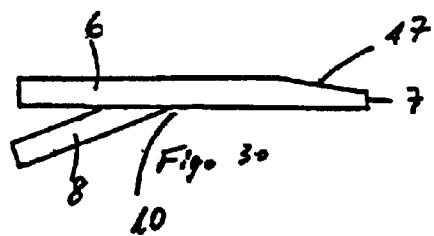
FIGS. 30–32 are schematic representations of a side view and two front views (taken at the ends) of a variant of the washing device of FIG. 3.
Figure 31:
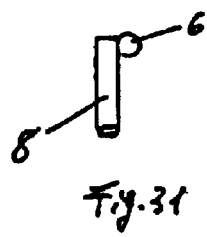
Figure 32:
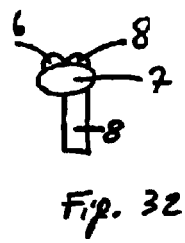

FIGS. 30–32 are schematic representations of a side view and two front views of a variant of the washing device 10 of FIG. 3, from which it differs exclusively in that the discharge channel 8 is set alongside the inlet channel 6. To FIGS. 30–32 apply (with possible variants that are obvious for a person skilled in the branch) all the considerations previously developed with reference to FIGS. 15–17.

Figure 33:
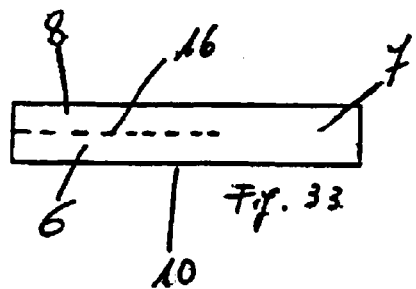
FIG. 33 is a schematic top view of the washing device of FIG. 24.

FIG. 33 is a schematic representation of a top view of the washing device 10 of FIG. 24. FIG. 33 shows, in a see-through view, the discharge channel 8 set alongside the inlet channel 6 (from which it is divided by the septum 16), and the end portion 7 of the inlet channel 6.

FIGS. 34–37 are schematic representations of a washing device 10 made according to the invention associated to means for supplying the washing liquid, which are designed to be normally used by specialized health personnel and the use of which involves (or may involve) serious risks of damage to the tympanic membrane 3 and/or may irritate the walls 4 of the external auditory meatus 2 if used (improperly) for self-washing of the external auditory meatus 2.

Figure 34:
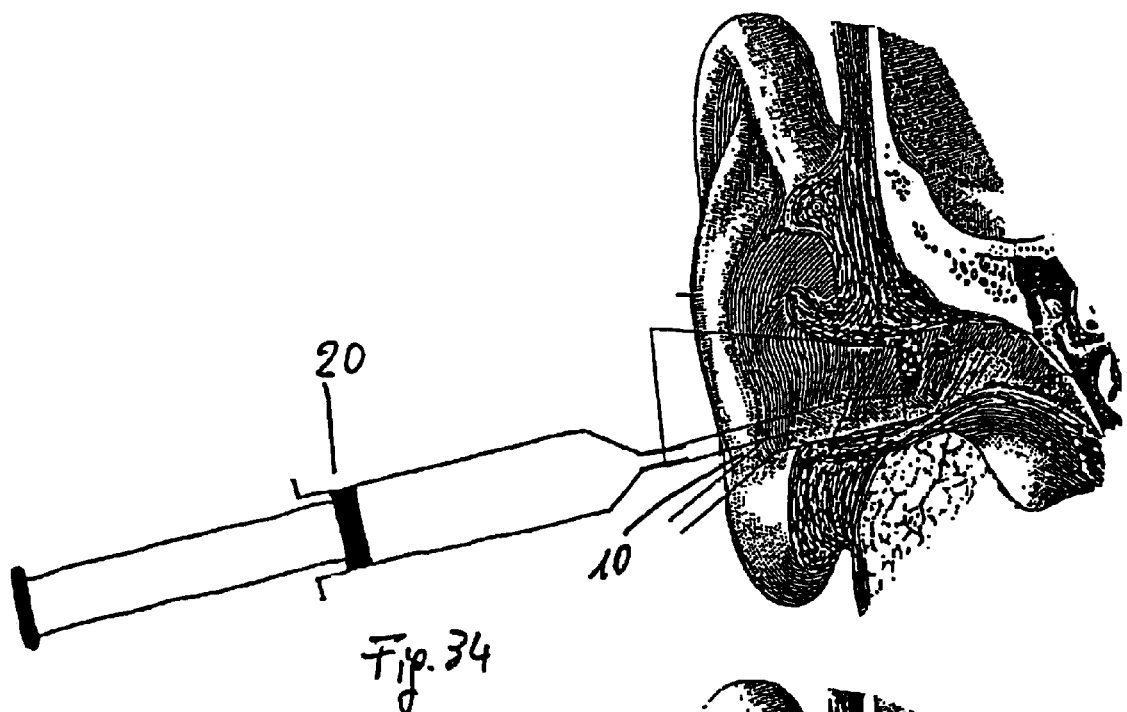
FIGS. 34–37 are schematic representations of a washing device made according to the invention associated to means (20, 21) designed to supply the washing liquid.
Figure 35:
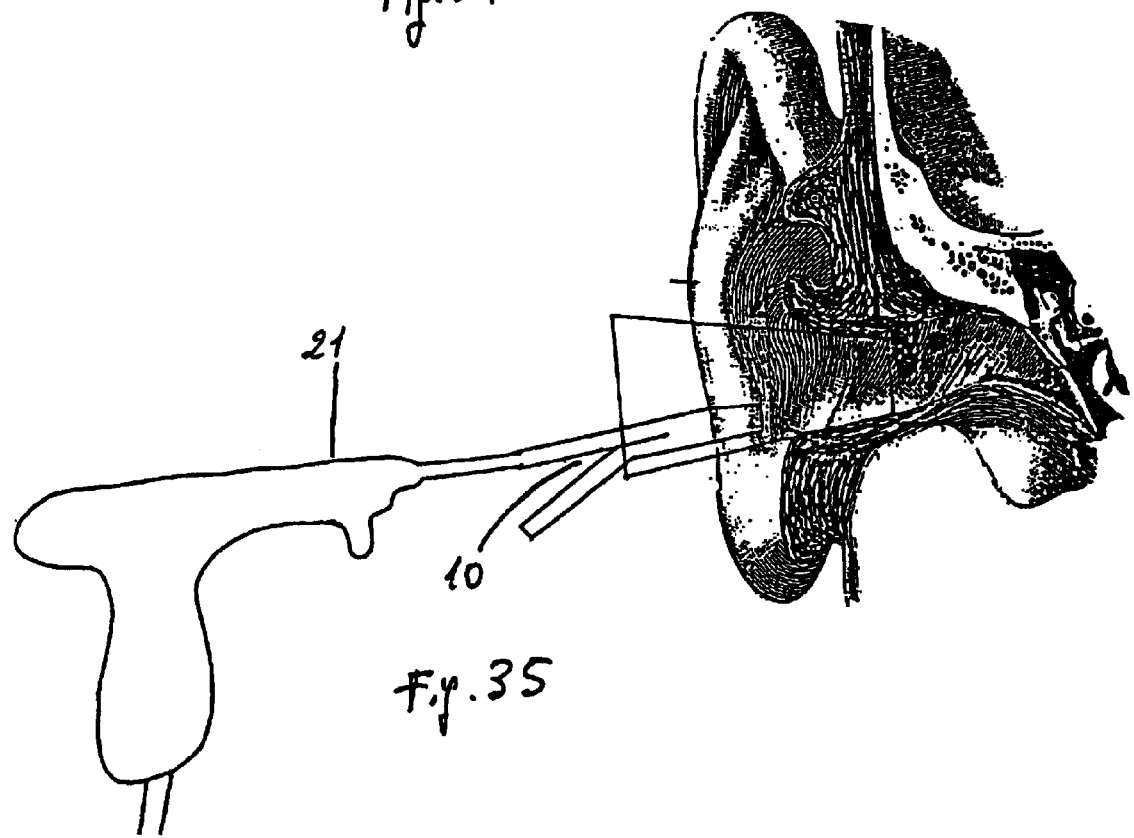
Figure 36:
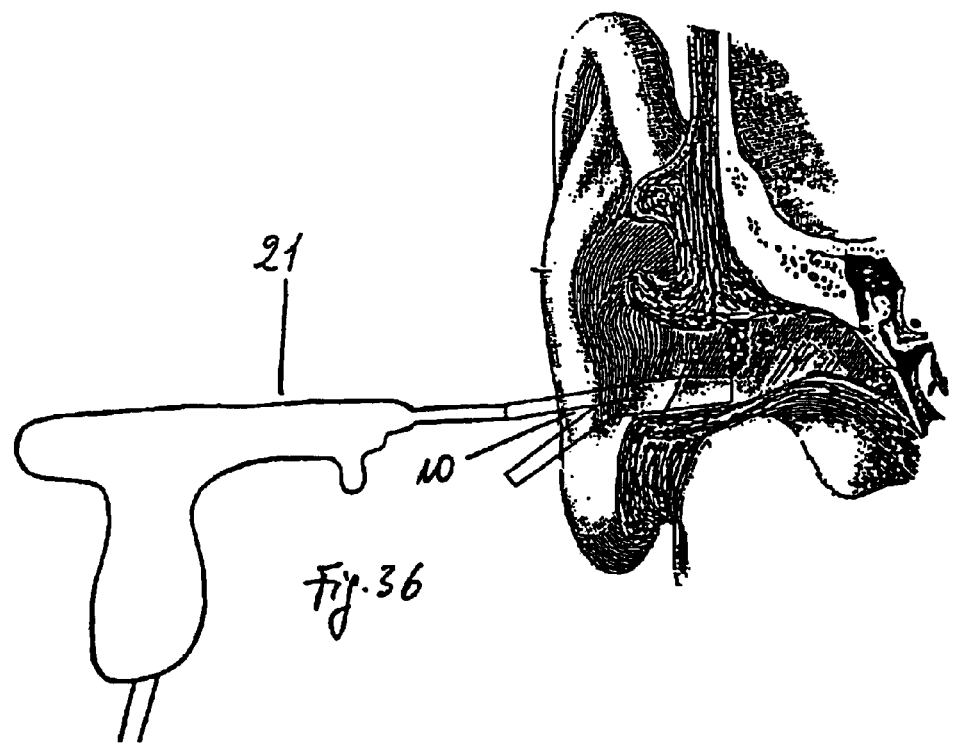
Figure 37:
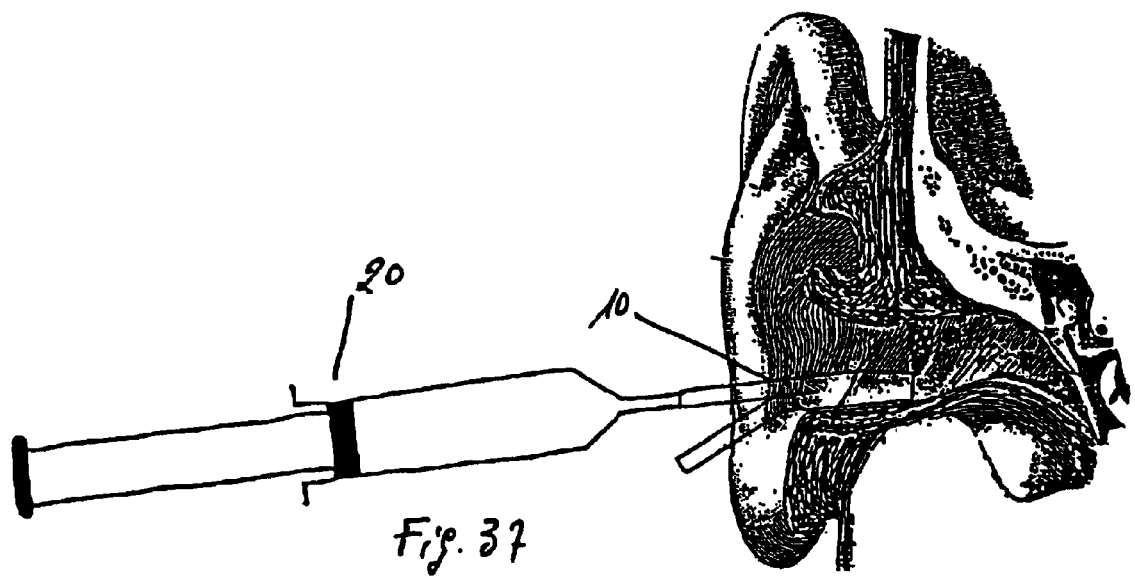

FIG. 34 shows a washing device 10 like the one illustrated in FIG. 5 associated to a syringe 20. FIG. 35 shows a washing device 10 like the one illustrated in FIG. 3 inserted in an aural speculum like the one illustrated in FIG. 2 and associated to a "spray gun" 21. FIGS. 36 and 37 illustrate a washing device 10 like the one illustrated in FIG. 3, in the case of FIG. 36 the washing device 10 being associated to a "spray gun" 21, and in the case of FIG. 37 the washing device 10 being associated to a syringe 20.

Finally, it is pointed out that a washing device 10 made according to the invention may be advantageously used as a means for inspection of the external auditory meatus 2 and/or of the tympanic membrane 3 in a device for self-viewing of the external auditory meatus 2 and/or of the tympanic membrane 3 like the ones described (merely to provide a non-limiting example) in the co-pending Italian patent application No. M199A000036 filed on Jan. 12, 1999.

Without departing from the scope of the invention, it is possible for a person skilled in the branch to make to the device 10 for washing the external auditory meatus that forms the subject of the present description all the modifications and improvements suggested by normal experience and by the natural evolution of techniques; for example, it is possible to provide two or more inlet channels 6 and/or two or more discharge channels 8.

What is claimed is:

1. A device for washing the external auditory meatus comprising;
   at least one inlet channel for the washing liquid, with an end portion;
   at least an output channel to discharge the washing liquid and the products of washing to the outside;
   wherein, it also comprises at least one discharge channel which connects the end portion of the at least one inlet channel directly to the outside, so as to discharge at least a portion of the washing liquid outside if said output channel is at least partially obstructed by the products of washing.

2. A device according to claim 1, wherein the output channel consists of an outlet channel made in the body of the washing device.

3. A device according to claim 1 inserted in an aural speculum, wherein said output channel consists of the portion of the aural speculum not occupied by the washing device.

4. A device according to claim 1, wherein the output channel consists of a space left free in the external auditory meatus.

5. A device according to claim 1, wherein the inlet channel is separated from the discharge channel by a septum, having a length shorter than that of the washing device, which delimits in addition the end portion of the inlet channel.

6. A device according to claim 5, wherein the section of the end portion of the inlet channel is greater than that of the initial portion of the inlet channel.

7. A device according to claim 5, wherein the discharge channel is not smaller than that of the initial portion of the inlet channel.

8. A device according to claim 5, wherein the inlet channel and the discharge channel are set one on the other.

9. A device according to claim 5, wherein the inlet channel and the discharge channel are set alongside one another.

10. A device according to claim 5, wherein the inlet channel and the discharge channel are parallel to one another.

11. A device according to claim 1, wherein the end portion of the discharge channel engages laterally in the body of the washing device, from which it projects.

12. A device according to claim 1, wherein the end portion of the discharge channel that protrudes from the body of the washing device constitutes the grip of the device itself.

13. A device according to claim 1, wherein the end portion of the discharge channel projecting from the body of the washing device is connected to a disposal container of the washing liquid that flows out of the discharge channel.

14. A device according to claim 1, wherein it includes, at the exit of the end portion of the inlet channel, means for deflecting the jet of liquid coming out of the washing device towards the wall of the external auditory meatus.

15. A device according to claim 14, wherein said means for deflecting direct and/or widen and/or flatten the jet of liquid coming out of the washing device.

16. A device according to claim 1, wherein the exit from the end portion of the inlet channel has an elliptical or flattened shape.

17. A device according to claim 1, wherein it is associated to a supplier of the washing liquid.

18. A device according to claim 1, for inspection of the external auditory meatus and of the tympanic in a device for self-viewing of the external auditory meatus and of the tympanic membrane.

* * * * *